US010183144B2

(12) United States Patent
Tang et al.

(10) Patent No.: US 10,183,144 B2
(45) Date of Patent: Jan. 22, 2019

(54) ULTRAVIOLET STERILIZING DRAINAGE CATHETER

(71) Applicants: The University of Maryland, Baltimore, Baltimore, MD (US); The United States of America as represented by the Department of Veterans Affairs, Washington, DC (US)

(72) Inventors: Cha-Min Tang, Wayne, PA (US); Paul E. Bigeleisen, Baltimore, MD (US); Samuel M. Galvagno, Jr., Baltimore, MD (US); Mark E. Shirtliff, Ellicott City, MD (US)

(73) Assignees: The University of Maryland, Baltimore, Baltimore, MD (US); The United States of America as represented by the Department of Veterans Affairs, Washington, DC (US)

( * ) Notice: Subject to any disclaimer, the term of this patent is extended or adjusted under 35 U.S.C. 154(b) by 949 days.

(21) Appl. No.: 14/535,296

(22) Filed: Nov. 6, 2014

(65) Prior Publication Data

US 2015/0126976 A1 May 7, 2015

Related U.S. Application Data

(60) Provisional application No. 61/900,420, filed on Nov. 6, 2013.

(51) Int. Cl.
*A61M 1/00* (2006.01)
*A61M 25/00* (2006.01)
*A61L 29/06* (2006.01)

(52) U.S. Cl.
CPC ......... *A61M 25/0043* (2013.01); *A61L 29/06* (2013.01); *A61M 25/0012* (2013.01);
(Continued)

(58) Field of Classification Search
CPC .......... A61M 25/0043; A61M 25/0012; A61M 25/0017; A61M 25/0045;
(Continued)

(56) References Cited

U.S. PATENT DOCUMENTS 9,358,369 B1* 6/2016 Webler, Jr. ......... A61B 1/00163
2003/0211022 A1* 11/2003 Gross ..................... C02F 1/325
422/292

(Continued)

OTHER PUBLICATIONS

Bak, Jimmy, et al., "A UVC Device for Intra-luminal Disinfection of Catheters: In Vitro Tests on Soft Polymer Tubes Contaminated with Pseudomonas aeruginosa, Staphylococcus aureus, Escherichia coli and Candida albicans", "Photochemistry and Photobiology", 2011, pp. 1123-1128, vol. 87, No. 5, Publisher: American Society of Photobiology, Published in: http://onlinelibrary.wiley.com/doi/10.1111/j.1751-1097.2011.00962.x/abstract.

(Continued)

*Primary Examiner* — Ariana Zimbouski
(74) *Attorney, Agent, or Firm* — Eugene J. Molinelli; Cian G. O'Brien; Beusse Wolter Sanks & Maire

(57) ABSTRACT

A device disclosed herein includes a tubular member which is flexible and configured to receive ultraviolet (UV) light from a UV illumination coupler. The tubular member contains a lumen defining a longitudinal interior space within the tubular member, a tubular body bounded by an inner wall defining an outer boundary of the lumen and an outer wall defining an outer surface of the tubular member, at least one optical fiber disposed outside of the interior space not parallel to an axis of the lumen and adapted to receive the UV light from the UV illumination coupler, and a protective component adapted to prevent substantially all of the UV light emitted from the optical fiber from exiting the outer wall. Methods for producing and using such devices are also disclosed herein.

19 Claims, 16 Drawing Sheets

(52) U.S. Cl.
CPC .... *A61M 25/0017* (2013.01); *A61M 25/0045* (2013.01); *A61M 2025/0056* (2013.01); *A61M 2202/0496* (2013.01); *Y10T 29/49016* (2015.01)

(58) Field of Classification Search
CPC .. A61M 2025/0056; A61M 2202/0496; A61M 2039/0285; A61L 29/06; A61L 2/10; A61L 9/20; Y10T 29/49016; G21K 5/10; A23L 3/26; A23L 3/28; A61B 18/22; A61B 18/24; C01F 1/325; C01F 1/32
See application file for complete search history.

(56) References Cited

U.S. PATENT DOCUMENTS

| | | | |
|---|---|---|---|
| 2004/0200976 A1* | 10/2004 | Yagi | G01J 1/42 250/372 |
| 2005/0256447 A1* | 11/2005 | Richardson | A61B 5/14539 604/65 |
| 2006/0195165 A1* | 8/2006 | Gertner | A61N 5/0603 607/86 |
| 2007/0219600 A1* | 9/2007 | Gertner | A61N 5/0603 607/88 |
| 2008/0095661 A1* | 4/2008 | Kohler | A61L 9/20 422/20 |
| 2008/0134899 A1* | 6/2008 | Subbarao | A61L 9/20 96/224 |
| 2011/0160681 A1 | 6/2011 | Dacey, Jr. et al. | |
| 2012/0161032 A1 | 6/2012 | Arcand et al. | |
| 2012/0197237 A1* | 8/2012 | Holzbauer | A61F 5/441 604/540 |
| 2013/0060188 A1* | 3/2013 | Bedwell | A61L 2/0047 604/21 |
| 2014/0320819 A1* | 10/2014 | Muller | A61B 3/0008 351/221 |

OTHER PUBLICATIONS

Bak, Jimmy, and T. Begovic, "A prototype catheter designed for ultraviolet C disinfection", "Journal of Hospital Infection", 2013, pp. 173-177, vol. 84, No. 2, Publisher: Elsevier, Published in: http://www.journalofhospitalinfection.com/article/S0195-6701%2813%2900112-6/pdf.

Dai, Tianhong, et al., "Ultraviolet C irradiation: an alternative antimicrobial approach to localized infections?", "Expert Rev Anti Infect There", 2012, pp. 185-195, vol. 10, No. 2, Publisher: Informa PLC, Published in: http://informahealthcare.com/doi/pdf/10.1586/eri.11.166.

Gadelmoula, Mostafa, et al., "Suitability of ultraviolet (A)-light emitting diode for air stream disinfection", "Journal of Medical Investigation", 2009, pp. 150-156, vol. 56, Publisher: University of Tokushima School of Medicine, Published in: http://medical.med.tokushima-u.ac.jp/jmi/vol56/pdf/v56_n3-4_p150.pdf.

Hall, Keri K., et al., "Ultraviolet Light Disinfection of Hospital Water for Preventing Nosocomial Legionella Infection: A 13-Year Follow-Up", "Invection Control and Hospital Epidemiology", 2003, pp. 580-583, vol. 24, No. 8, Publisher: University of Chicago Press, Published in: http://www.jstor.org/stable/10.1086/502257? origin=JSTOR-pdf.

Hijnen, W. A. M., et al., "Inactivation credit of UV radiation for viruses, bacteria and protozoan (oo)cysts in water: A review", "Water Research", 2006, pp. 322, vol. 40, Publisher: Elsevier, Published in: www.elsevier.com/locate/watres.

Kolappan, A., and S. Satheesh, "Efficacy of UV Treatment in the Management of Bacterial Adhesion on Hard Surfaces", "Polish Journal of Microbiology", 2011, pp. 119-123, vol. 60, No. 2, Publisher: Polish Society of Microbiologists, Published in: http://www.pjm.microbiology.pl/.

Norval, Mary, "The Effect of Ultraviolet Radiation on Human Viral Infections", "Photochemistry and Photobiology", 2006, pp. 1495-1504, vol. 82, Publisher: American Society for Photobiology, Published in: http://onlinelibrary.wiley.com/doi/10.1111/j.1751-1097.2006.tb09805.x/pdf.

Shimomura, Akira et al., "The Effect of Ultraviolet Rays on the Prevention of Exit-Site Infections", "Advances in Peritoneal Dialysis", 1995, pp. 17, vol. 11, No. 3, Publisher: International Society for Peritoneal Dialysis, Published in: http://www.advancesinpd.com.

Vermeulen, Natasha, et al., "The Bactericidal Effect of Ultraviolet and Visible Light on *Escherichia coli*", "Biotechnology and Bioengineering", 2007, pp. 550-556, vol. 99, No. 3, Publisher: Wiley Periodicals, Published in: www.interscience.wiley.com.

* cited by examiner

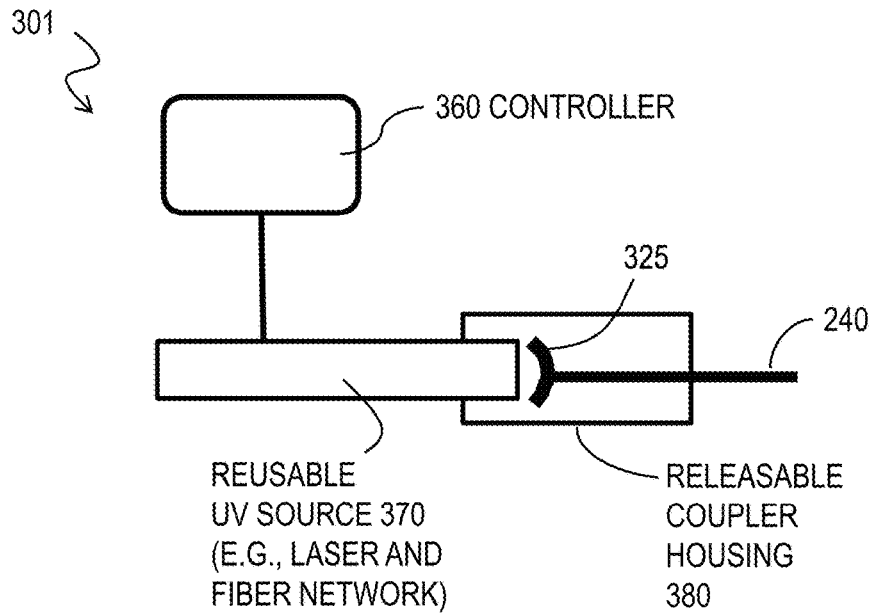
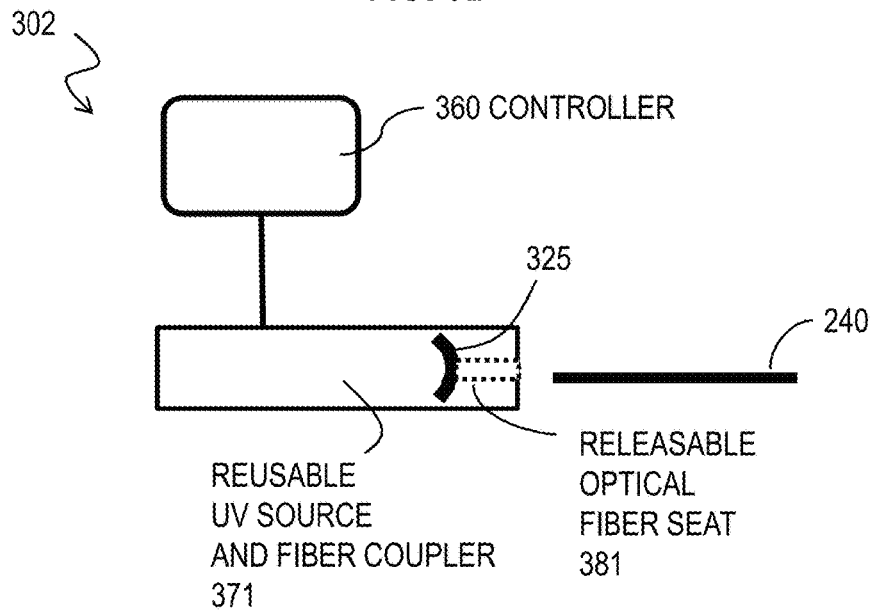

OPTICAL COUPLER
(PRIOR ART)

OPTICAL COUPLER
(PRIOR ART)

OPTICAL COUPLER
(PRIOR ART)

ULTRAVIOLET STERILIZING DRAINAGE CATHETER

CROSS-REFERENCE TO RELATED APPLICATIONS

This application claims benefit of Provisional Application No. 61/900,420, filed Nov. 6, 2013, the entire contents of which are hereby incorporated by reference as if fully set forth herein, under 35 U.S.C. § 119(e).

BACKGROUND

Catheter associated urinary tract infections (CAUTIs) are a common problem for those with indwelling urinary catheters. It is observed that over 70% of urinary catheters become colonized with bacteria over a relatively short period of time. Bacteria colonization is often accompanied by the formation of a biofilm that is known to sustain bacterial growth and to also increase the likelihood of infection.

Various approaches have been employed to reduce urinary tract infections associated with the use of indwelling urinary catheters. Common interventions such as silver alloy coatings, antimicrobial catheter coatings, hydrophilic catheters, ureteral stents, use of sealed catheter-tube junctions, and anti-infective bladder irrigation have yielded inconsistent results in reducing the incidence of CAUTI. The deficiencies associated with these and other common interventions are especially troubling in light of the emergence of antimicrobial-resistant organisms such as multi-drug resistant (MDR) organisms which are becoming more prevalent.

Ultraviolet (UV) irradiation has long been recognized for its potential to destroy viruses, bacteria, fungi, and other harmful microorganisms. Application of UV radiation is known to sever carbon-carbon double bonds in genetically-relevant organic moieties (e.g., pyrimidines, purines and flavanoids). Susceptibility to UV irradiation occurs when dimers (uracil and cytosine in ribonucleic acid, RNA, and thymine and cytosine in deoxyribonucleic acid, DNA) are formed.

Based upon this finding, some catheter devices have been designed to allow in situ sterilization of catheter elements and surrounding tissues by transmitting UV radiation through indwelling elements. Arcand et al. (WO 2010/132429), for example, describes an elongated catheter insertion device that includes an integrated UV sterilization assembly providing both inward-directed (toward the interior of the device) and outward-directed (toward the exterior of the device into surrounding tissue) UV irradiation. Such a device does not penetrate far into the subject's body, and is intended to irradiate an instrument, such as a needle or catheter, as the instrument passes through the device. In another example Kaldany (U.S. Pat. No. 5,695,482) describes catheter tubes capable of in situ UV sterilization in which linear fiber optics embedded in walls of a catheter tube allow multi-directional UV radiation of both the catheter interior and the surrounding tissue.

Common forms of UV radiation known to destroy harmful microorganisms include UVA (315 to 400 nm), UVB (280 to 315 nm) and UVC (100 to 280 nm) radiation. However, all forms of UV light can also produce DNA damage in mammalian cells and are potentially harmful to the tissues being penetrated by the catheter. A clear link exists between chronic exposure to UV light and skin cancer resulting from UV-induced damage to DNA.

SUMMARY

Applicants recognize that a need exists to discover methods and apparatuses for reducing the threat of catheter associated urinary tract infection (CAUTI) during use of indwelling drainage catheters. Ideal methods and apparatuses would be effective at sterilizing catheter components—or otherwise reducing levels of bacteria and other microorganisms (collectively referenced as infective agents) to prevent CAUTIs—while at the same time protecting bodily tissues and other objects against exposure to potentially-harmful forms of radiation. A need also exists to apply similar methods and apparatuses to other indwelling and non-indwelling devices in which device self-sterilization is desirable but exposure of vulnerable tissues and other objects to potentially-harmful forms of radiation is not desirable.

Applicants discovered methods and apparatuses that reduce or prevent intra-luminal growth of bacteria and other harmful microbes by using optical fibers and reflective materials to control the direction and intensity of UV light being applied to device internals—while at the same time reducing or eliminating UV light directed towards sensitive tissues and objects, and keeping the catheter flexible enough to follow the contours of a body lumen of the subject. As used herein, a subject is a human or animal whose body lumen is to be penetrated by a catheter for the passage of fluids or solids in either direction into or out of the subject.

One set of embodiments relates to a device comprising a tubular member. The tubular member is flexible and configured to receive ultraviolet (UV) light from a UV illumination coupler. The tubular member comprises a lumen defining a longitudinal interior space within the tubular member, a tubular body that is bounded by an inner wall defining an outer boundary of the lumen and an outer wall defining an outer surface of the tubular member, at least one optical fiber disposed outside of the interior space not parallel to an axis of the lumen and adapted to receive UV light from the UV illumination coupler and to emit UV light along at least a portion of a length of the lumen, and a protective component adapted to prevent substantively all of the UV light emitted from the optical fiber from exiting the outer wall.

Another set of embodiments relates to a method for producing a device containing a UV illumination coupler and a tubular member. The method comprises affixing at least one optical fiber to a flexible material to form a fiber-containing structure, rolling the fiber-containing structure to form a rolled structure defining a hollow space corresponding to an interior space of a lumen, sealing the rolled structure to form a tubular member, and attaching the UV illumination coupler to the tubular member.

Another set of embodiments relates to a treatment method using a device containing a UV illumination coupler and a tubular member. The treatment method comprises inserting a distal end and a portion of a tubular member into a body cavity, duct or vessel of a subject, passing a liquid or a solid object through a lumen contained in the tubular member, and transmitting a UV light through the UV illumination coupler to illuminate at least a portion of the longitudinal interior space with sufficient dose of UV light to inactivate a therapeutically effective amount of infective agents.

Still other aspects, features, and advantages of the invention are readily apparent from the following detailed description, simply by illustrating a number of particular embodiments and implementations, including the best mode contemplated for carrying out the invention. The invention is also capable of other and different embodiments, and its several details can be modified in various obvious respects, all without departing from the spirit and scope of the invention. Accordingly, the drawings and description are to be regarded as illustrative in nature, and not as restrictive.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 3A-3C are block diagrams illustrating examples of UV illumination systems, according to some embodiments;

DETAILED DESCRIPTION

Figure 1:
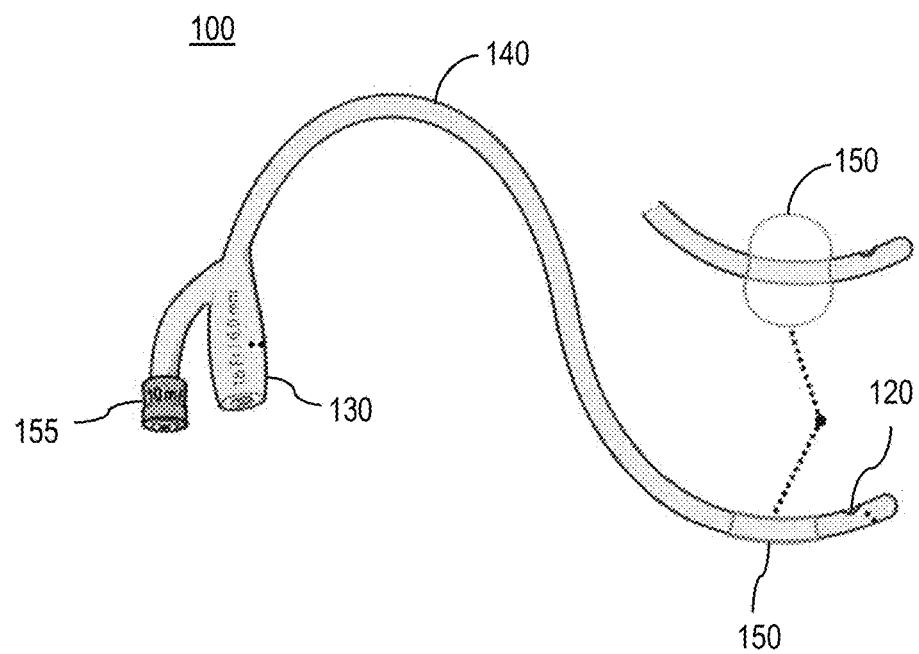
FIG. 1 depicts a standard indwelling catheter.

Self-sterilizing indwelling catheters and other self-sterilizing devices are provided for herein—as well as methods for producing and using these devices. In the following description, for the purposes of explanation, numerous specific details are set forth in order to provide a thorough understanding of the present invention. It will be apparent, however, to one skilled in the art that the present invention may be practiced without these specific details. In other instances, well-known structures and devices are shown in block diagram form in order to avoid unnecessarily obscuring the present invention.

Applicants discovered methods and apparatuses that reduce or prevent intra-luminal growth of bacteria and other harmful microbes. Devices of the present disclosure include optical fibers and reflective materials adapted to control the direction and intensity of UV light being applied to device internals. Use of at least one reflective material allows UV light transmitted through at least one optical fiber to be directed inward in order to irradiate intra-luminal regions where bacterial colonies tend to congregate. Consequently, exposure of outwardly-disposed tissues and objects may be eliminated or reduced to a desired level.

While some embodiments of the invention are described below in the context of self-sterilizing indwelling catheters suitable for lowering the risk of catheter associated urinary tract infection (CAUTI), the invention is not limited to this context. It should be understood that the methods and apparatuses described herein may be used in a wide range of applications requiring the transmission and directionally-selective irradiation of UV light. These may include, for example, non-urinary processes and apparatuses such as peritoneal dialysis systems, gastrointestinal tubes (such as nasogastric tubes and feeding tubes), intravenous devices (e.g., central venous catheters, intravenous catheters, implanted blood access devices, vascular shunts for hemodialysis, peripherally inserted central catheters, percutaneous, implanted, long-term intravascular catheters), membrane lung for long-term pulmonary support (e.g., extracorporeal blood oxygenation), oropharyngeal airway tubes (e.g., endotracheal tubes), tracheobronchial suction catheters, cerebrospinal fluid shunts and drains, devices for vacuum-assisted closure (also called vacuum therapy, vacuum sealing or topical negative pressure therapies), colostomy bags and tubing, catheters and tubing associated with the subcutaneous administration of insulin or other mediations, Swan-Ganz catheters, and umbilical lines, for the administration of fluids and blood, removing/replacing fluids and blood, or storage and fluid transfer devices for handling of blood and other fluids. Also, many embodiments are described to include specific mechanical and electrical, as well as specific materials employed in these components. But other embodiments may include additional components and materials or modified components and materials. One having ordinary skill in the art would recognize minor changes that may be necessary to adapt the methods and apparatuses described herein for different uses. These modifications should be considered part of the present disclosure because they do not depart from the overall spirit.

FIG. 1 illustrates a generic double lumen indwelling urinary tract catheter that may be adapted according to the present disclosure to control the direction and intensity of UV light applied to the device internals. The term "catheter" is used herein in a general sense to describe a flexible tube with a hollow lumen capable of being passed into a body lumen and passing fluids longitudinally through the tube. Catheter 100 has a urine drainage port 130 at the proximal end and an opening 120 at the distal end. The opening and drainage port communicate with each other by way of a central lumen 140 that runs the length of the catheter. In the depicted embodiment, a balloon 150 is located near the distal end of the catheter, and a balloon port 155 in fluid communication with the balloon 150 is located at the proximal end. The balloon port 155 is used to inflate the balloon 150 so that the catheter 100 does not slip out of the bladder.

In various embodiments, the catheter length is adapted for the body lumen and access thereto. For example, in some embodiments, a length of the catheter 100 ranges from about 4 cm to about 100 cm. In other embodiments, a length of the catheter 100 ranges from about 5 cm to about 50 cm. In still other embodiments, a length of the catheter 100 ranges from about 5 cm to about 30 cm. In yet other embodiments, a length of the catheter 100 ranges from about 10 cm to about 25 cm. In still other embodiments, a length of the catheter 100 is about 20 cm.

Figure 2A:
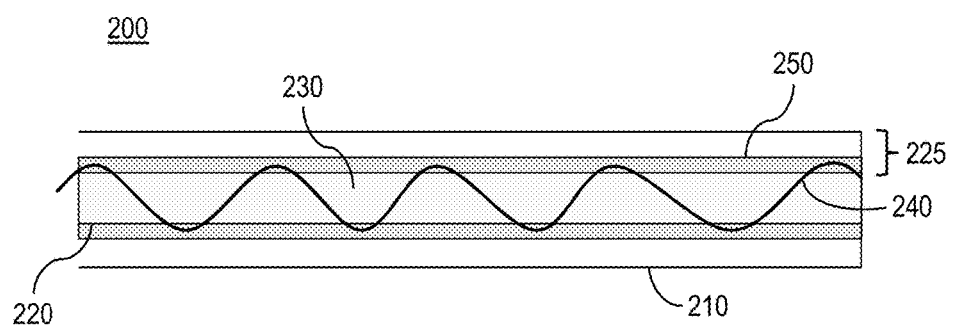
FIGS. 2A and 2B are block diagrams that illustrate cross-sectional views of an example tubular member, according to an embodiment.
Figure 2B:
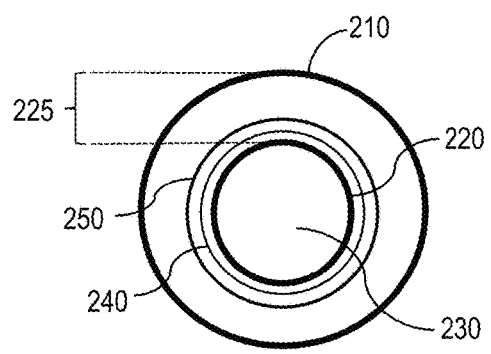

As explained above, a generic catheter such as that depicted in FIG. 1 may be modified according to the present disclosure to control the direction and intensity of UV light that may be applied to the device internals. FIGS. 2A and 2B are block diagrams that illustrate cross-sectional views of an example tubular member, according to an embodiment. FIG. 2A illustrates a longitudinal cross section of an example tubular member 200. FIG. 2B depicts an axial cross section of the example tubular member 200 of FIG. 2A. Tubular member 200 comprises an outer wall 210 and an inner wall 220. An area of the tubular member 200 bounded by the outer wall 210 and the inner wall 220 may be referred to as a tubular body 225. A lumen 230 is located inside tubular member 200 and extends from the proximal drainage port 130 to the distal opening 120 (see FIG. 1). One or more optical fibers 240 are located within tubular member 200 and extend at least a portion of the length of the catheter 100.

Although the embodiment described above is an adapted version of the catheter 100 of FIG. 1, the present disclosure is not limited to include the features shown in FIG. 1. In other embodiments, for example, the tubular member 200 may be a more simplified version having holes at the distal and proximal ends for ingress and egress of fluids. In some embodiments, an exterior surface of the catheter, or a portion thereof, is coated with a composition that retards biofilm growth, using any composition known in the art.

The term "optical fiber" is used herein in a general sense to describe a flexible, transparent fiber made of a light-transmitting material. The optical fiber 240 may be disposed in a variety of configurations within the tubular member 200. In the non-limiting embodiment of FIG. 2A, one optical fiber 240 is a spiral-shaped optical fiber that wraps around the lumen 230 in an essentially coaxial configuration. A spiral-shaped optical fiber 240 may encircle an entire circumference of the lumen 230 or may only partially encircle the lumen 230. A spiral-shaped optical fiber 240 may encircle an entire circumference of the lumen 230 one or more times over the length of the tubular member 200. In other embodiments the optical fiber can be in any configuration that is not parallel to the axis of the lumen. It is a disadvantage to dispose optical fibers in a straight linear fashion parallel to the axis of the lumen because optical fibers can bend but cannot stretch and thus the axial linear arrangement is mechanically weak. If two optical fibers were placed in linear axial arrangement, they would break when bent in any plane other than that perpendicular to the plane of the two fibers. Thus, in many embodiments the optical fibers are disposed in a curved configuration in the catheter. Fibers may be adapted in some embodiments to be flexible optical fibers capable of being flexed as part of a flexible tubular member 200. Some embodiments include multiple optical fibers including, for example, multiple optical fibers that are disposed in substantively parallel curved bundles through the tubular member 200.

In some embodiments the optical fiber is in the form of one or more diffusive optical fibers. The term "diffusive optical fiber" is used herein in a general sense to describe optical fibers designed to direct a portion of light radially from the longitudinal axis of the fiber. This may be achieved through the placement of light scattering elements contained within the diffusive optical fibers. The resulting effect is the diffuse illumination of a large length of the optical fiber from light inputted from one of its ends. Diffusive optical fibers may also be achieved through the choice of at least one light transmitting material having a different index of refraction in order to regulate the degree of total internal reflection within the optical fibers. Some optical fibers are configured to reduce loss along the length and deliver a large fraction of the light input at one end to the other end. In some embodiments, as described below with reference to FIG. 14, such fibers are terminated within the lumen to emit light along the portion of the length of the lumen in the vicinity of the terminus. In some embodiments diffusive optical fibers as used herein are configured to let light escape along the length, often at a specified rate. In various embodiments, the optical fiber 240 includes at least a portion of a diffusive optical fiber where the interior lumen is to be illuminated, with or without non-diffusive optical fiber to deliver light to the diffusive portion without excessive loss.

The optical fiber 240 illustrated in FIG. 2A is configured as a spiral-shaped optical fiber wrapped within a portion of the tubular body 225 containing an interior space of the lumen 230. In other embodiments, tubular members 200 of the present disclosure may include more than one optical fiber 240 each configured in the shape of overlapping or non-overlapping spirals. In other cases the one or more optical fiber 240 may be configured in the shape of overlapping or non-overlapping geometric shapes effective to control the shape and intensity of UV light applied to the interior space of the tubular member 200. It is advantageous that the optical fiber is not parallel to the axis of the lumen, because such configurations are subject to breakage when the tube is bent to traverse along a body lumen. Optical fiber can bend but does not stretch. The one or more optical fibers 240 may be located on the face of the inner wall 220, or may be embedded between the inner wall 220 and outer wall 210 in the tubular body 225.

Figure 13A:
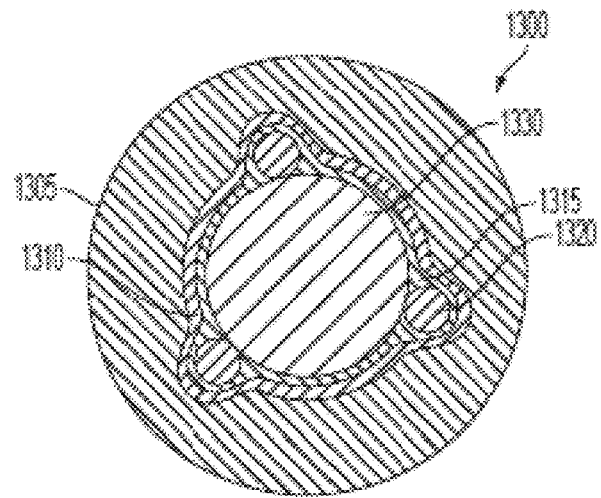
FIGS. 13A and 13B are block diagrams that illustrate transverse cross-sectional views of example tubular members, according to embodiments.
Figure 13B:
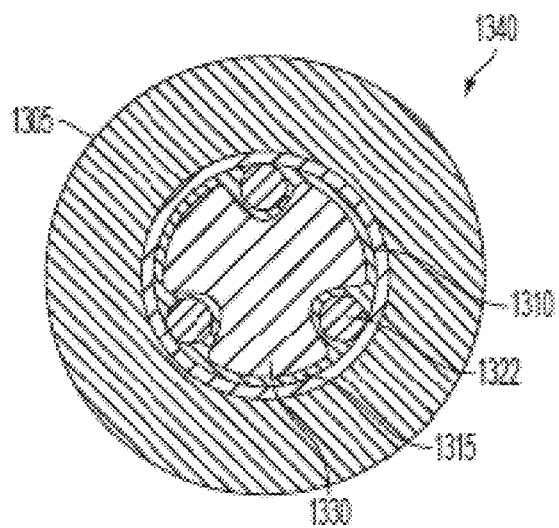

FIGS. 13A and 13B are block diagrams that illustrate cross-sectional views of example tubular members 200, according to embodiments. FIG. 3A is a block diagram that illustrates an axial cross-sectional view 1300 of an example tubular member 200, according to an embodiment, in which more than one optical fiber or bundle 1320 are embedded within the tubular body 225 of a tubular member 200. The optical fibers/bundles 1320 are embedded within a UV transmitting material 1315 of the inner wall 220 of the lumen 1330, and are surrounded by a UV reflective coating 1310 which is itself surrounded by a flexible catheter material 1305 (often made of UV absorbent plastic material such as a polyurethane) to form a smooth-bore inner surface 220. FIG. 13B is a block diagram that illustrates an axial cross-sectional view 1340 of an example tubular member 200, according to an embodiment, in which more than one optical fiber or bundle 1322 are embedded within the inner wall 220 of the lumen 1330. The optical fibers/bundles 1322 are embedded within a UV transmitting material 1315 of the inner wall 220 of the lumen 1330, and are surrounded by a UV reflective coating 1310 which is itself surrounded by a flexible catheter material 1305 that is UV absorbent, to form a non-smooth-bore inner surface 221.

Figure 14:
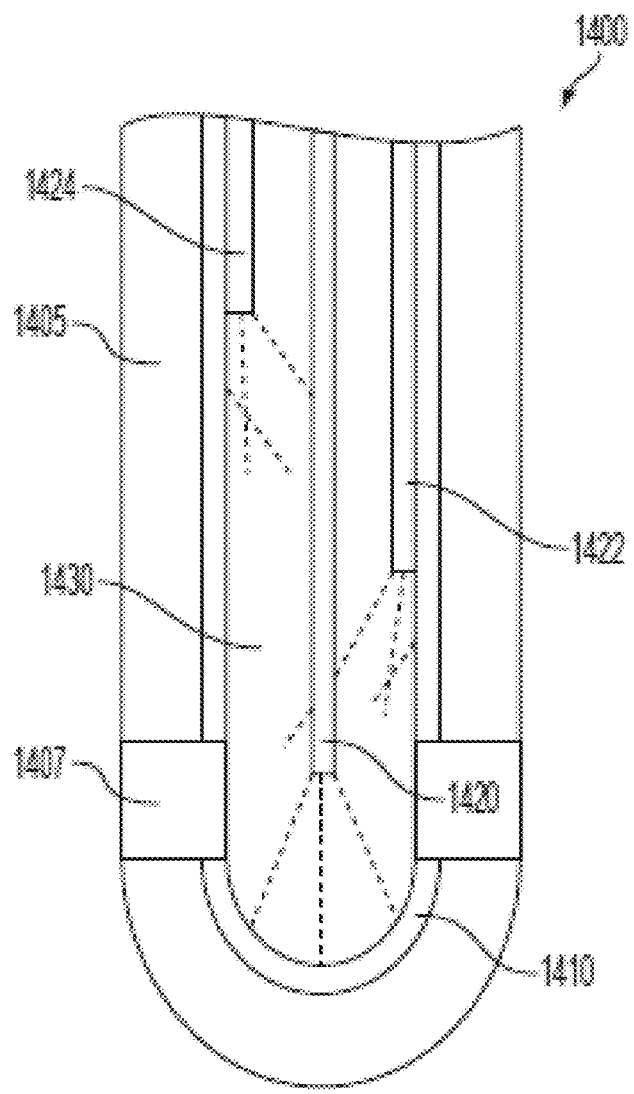
FIG. 14 is a block diagram that illustrates a longitudinal cross-sectional view of an example tubular member, according to an embodiment.

FIG. 14 is a block diagram that illustrates a longitudinal cross-sectional view 1400 of an example tubular member 200, according to an embodiment, in which more than one non-diffusive optical fiber or bundle are contained within the lumen 1430. The tubular member 200 contains a UV reflective inner surface 1410 surrounded by a flexible catheter material 1405, that is UV absorbent in some embodiments. The distal end of the tubular member 200 contains an opening 1407. In this embodiment three optical fibers 1420, 1422 and 1424 are disposed within the lumen 1430. A longest optical fiber/bundle 1420 is adapted to illuminate the distal end of the tubular member 200, a medial-length optical fiber/bundle 1422 is disposed along one side of the inner surface 220 and is adapted to illuminate a central portion of the tubular member 200, and a short-length optical fiber/bundle 1424 is disposed along another side of the inner surface 220 and is adapted to illuminate a proximal end of the tubular member 200. In various embodiments the optical fibers/bundles 1420, 1422 and 1424 may be diffusive optical fibers/bundles, non-diffusive optical fibers/bundles, or a combination thereof. Use of multiple optical fibers/bundles enables the intensity of UV illumination to be controlled throughout the longitudinal axis of the tubular member 200.

In some embodiments, the optical fiber 240 may have a diameter from about 50 microns to about 500 microns. In other embodiments, the diameter of the optical fiber 240 is about 50 microns to about 250 microns. In some cases the optical fiber may be in the form of a bundle of optical fibers wrapped together. In such embodiments, the one or more optical fibers 240 contained in the tubular member 200 may be in the form of one or more optical fiber bundles. The optical fibers within fiber bundles may be of different lengths and diameters and exhibit different leakage rates of UV light. Because the rate of light leakage may be controlled by using diffusive optical fibers, the combination of multiple optical fibers (e.g., fiber bundles) having different lengths and different rates of light leakage enables precise control of UV light illumination along the length of the tubular member 200.

In some embodiments, the one or more optical fiber 240 is constructed of a light transmissive core material having a relatively high index of refraction and surrounded by a cladding material having a relatively lower index of refraction. For example, in one embodiment, an optical fiber 240 included in the tubular member 200 contains a light transmissive core material having an index of refraction of about 1.62 and surrounded by a cladding material having an index of refraction of about 1.52. In some embodiments, the optical fiber 240 is a graded-index optical fiber in which the index of refraction in the core decreases continuously between the axis of the optical fiber and the boundary of the core with the cladding material. In some cases the cladding material may be a transparent cladding material, and in other cases the cladding material may be a translucent, light-absorptive or opaque cladding material. Additionally, a clear outer coating or buffer having a different index of refraction may be disposed around the optical fiber (to surround the fiber core and cladding) to further control the light leakage rate of the optical fiber. For example, in some embodiments the optical fiber may be surrounded by a clear silicone buffer serving as both a protective layer and a modulator of light leakage.

In some embodiments, the index of refractions of the core and the cladding of the optical fiber 240 are configured to achieve significant leakage of the ultraviolet light within about one to two meters from a point of UV illumination into the optical fiber 240. A typical leakage rate is about 10% per centimeter of the tubular member 200, but can be as little as about 1% per centimeter. In some embodiments, the leakage rate of the one or more optical fibers 240 can be a variable leakage rate that increases or decreases along the length of the tubular member 200. The specific index of refractions of the core and cladding for a given embodiment will depend on the length of the catheter 100 and the intensity of the UV source being applied to the one or more optical fibers 240.

In the non-limiting embodiments of FIGS. 2A and 2B, a UV reflective layer 250 is also located between the outer wall 210 and the one or more optical fibers 240. In other embodiments, the tubular member 200 may contain a UV reflective material which can eliminate the need for a distinct ultraviolet reflecting layer 250. Some tubular members 200 may contain both a UV reflective material and a UV reflective layer 250. In some embodiments, the UV reflective layer 250 may be in the form of a UV reflective coating forming the outer wall 210 of the tubular member 200. In other cases the UV reflective layer or material 250 may be situated between the one or more optical fibers 240 and the outer wall 210.

In some embodiments, the distal end of optical fiber 240 may also contain a reflective surface to reflect light reaching the distal of the optical fiber 24 end back into the catheter tube 200. Such a reflective surface may include a mirrored end of the optical fiber 240 formed, for example, using metallic deposition methods. In other embodiments, the reflective surface may be in the form of a dielectric coating. This reflective end is advantageous in reducing the light released into the subject, where UV light can damage healthy tissue, and instead direct that light back along the optical fiber when it can be directed into the lumen of the tubular body.

Materials employed as the UV reflective component or layer 250 include all materials known in the art which reflect UV light. In some embodiments, for example, the UV reflective component 250 may be a reflective-metal-containing coating. Reflective metals may include, for example, titanium, aluminum, chromium, iron, nickel, copper, zinc, palladium, silver, platinum and gold, to name a few. In some non-limiting embodiments, for example, the UV reflective component 250 may be an aluminum-containing coating that forms the outer wall 210. In some cases the aluminum-containing coating may be a coating of aluminum foil wrapped around the tubular member 200. An advantage of a reflective material or layer over a purely absorptive outer layer is that a reflective layer can more efficiently use the UV light emanating from the optical fiber. In other embodiments the UV reflective component 250 may be in the form of a UV reflective layer disposed within the tubular body 225 near the inner wall 220 but surrounding the optical fiber(s)/bundle(s) to confine UV light to the interior space of the lumen 230.

In various embodiments, materials contained in the tubular body 225 include UV transmissive materials or UV absorbent materials, or some combination. UV absorbent materials include most known plastics (such as polyurethane and latex) which absorb UV in the wavelength range of less than 300 nm. UV transmissive materials include silicones. In some embodiments, the materials contained in the tubular body 225 changes from the inner wall 220 to the outer wall 210. For example, in some non-limiting embodiments, the tubular body 225 comprises a UV transmissive inner section containing the one or more optical fibers 240 embedded in a UV transmissive material and situated at or near the inner wall 220, and a UV absorbent outer section containing a UV absorbent material and situated at or near the outer wall 210. In some cases the inner wall 220 is a flexible material which transmits UV light.

In some embodiments, the outer wall 210 of the tubular member 200 includes a protective coating adapted to release at least one oxidizing agent during operation of a device containing the tubular member 200. Suitable oxidizing agents include all known oxidizers used to sterilize indwelling catheters and may be, for example, nitric oxide, ozone, or a combination thereof. In some embodiments, the release of at least one oxidizing agent may be induced by interaction of the outside wall 210 with visible light. An advantage of such a coating is to kill bacteria or other infective agents on the outside wall of the catheter, which is not exposed to the UV light.

Figure 3C:
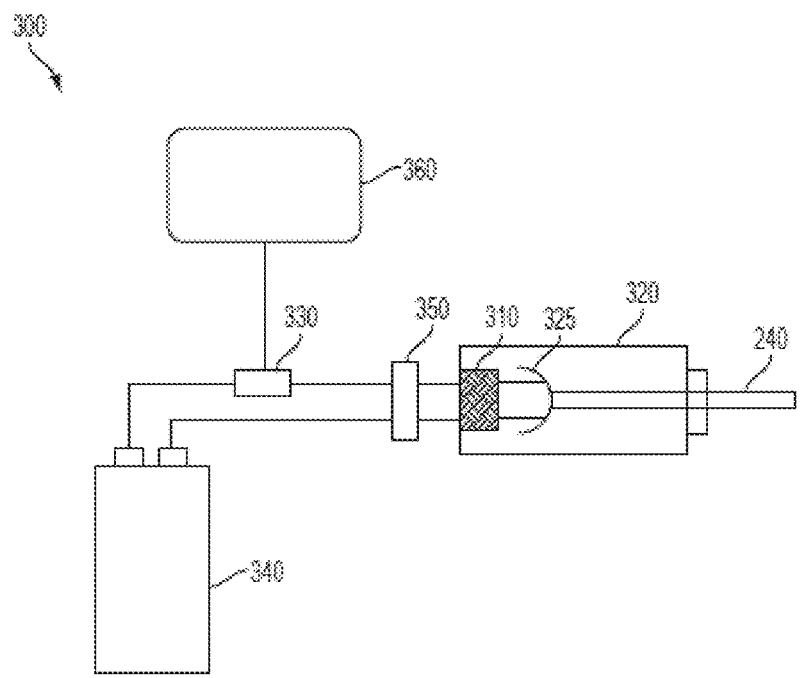

FIGS. 3A-3C are block diagrams illustrating examples of UV illumination systems, according to embodiments.

FIG. 3A is a block diagram that illustrates an example of a UV illumination system configuration 301, according to an embodiment, at the proximal end 130 of optical fiber/bundle 240. A reusable UV source 370 (e.g., laser and fiber network) with a UV-fiber coupler 325 in a releasable coupler housing 380 is used to illuminate optical fiber/bundle 240. In some embodiments, the UV illumination system 301 may also contain a controller 360 adapted to provide on/off and intensity control of one or more UV sources 370.

FIG. 3B is a block diagram that illustrates an example of a UV illumination system configuration 302, according to an embodiment, at the proximal end 130 of optical fiber/bundle 240. A reusable UV source and fiber coupler 371 with a UV-fiber coupler 325 includes a releasable optical fiber seat 381, and is used to illuminate optical fiber/bundle 240. In some embodiments, the UV illumination system 302 may also contain a controller 360 adapted to provide on/off and intensity control of one or more UV sources 371.

FIG. 3C is a block diagram that illustrates an example of a UV illumination system configuration 300, according to an embodiment, at the proximal end 130 of optical fiber/bundle 240. A UV source 310, such as a light-emitting diode (LED), housed with a UV-fiber coupler 325 in housing 320 is used to illuminate optical fiber/bundle 240. A socket 350 connects the UV source 310 to a power source 340 and a current controller 330. In some embodiments, the UV illumination system 300 may also contain a controller 360 adapted to provide on/off and intensity control of one or more UV sources 310.

The UV source 310 may be selected from at least one of a mercury lamp, a xenon lamp, a light emitting diode (LED), a laser diode (LD), a superluminescent LED (SLED), a nanodot LED, a quantum dot and a combination thereof.

Figure 4:
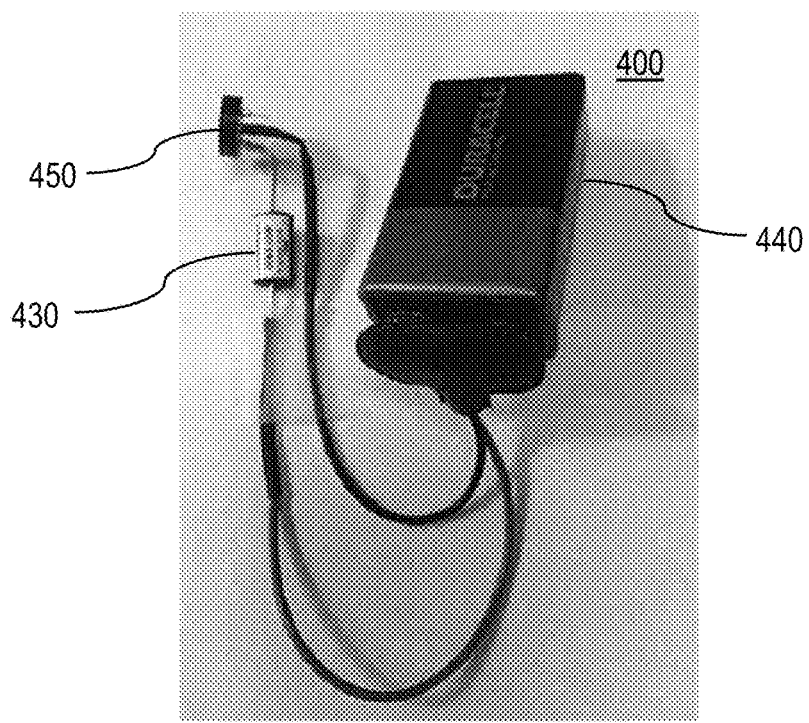
FIG. 4 is a photograph that illustrates an example of a power supply, according to an embodiment.

FIG. 4 is a photograph that illustrates an example of a power supply 400, according to an embodiment. In the illustration of FIG. 4, for example, a battery 440 is used as the power source, and the battery 440 provides current to socket 450 via a current controller 430. However, any other power source capable of generating the required current to power the UV source 310 may be used.

Ultraviolet LEDs that produce light at wavelengths less than about 300 nm may be used as the UV source 310. In certain embodiments, the UV source 310 transmits UV light having a wavelength between about 250 nm and about 300 nm, or between about 250 nm and about 280 nm. In other cases the UV source 310 transmits UV light having a wavelength between about 260 nm and about 280 nm. In some embodiments the UV light is UVA, UVB and/or UVC light. The UV source 310 may be in the form of one or more LEDs, laser diodes (LD), a superluminescent LED (SLED), nanodot LEDs, or quantum dots transmitting UV light in the ranges listed above, as well as a mercury lamp or a xenon lamp. For example, nanodots may be embedded within the tubular member 200 enabling the transmission of visible light via the one or more optical fibers 240 to produce site-directed UV light in situ at specific locations in the tubular member 200. In some embodiments nanocrystals may be applied to the inner wall 220 or embedded within the tubular body 225 such that a non-toxic visible light may be transmitted through the tubular member 200 and upconverted into UV light by the nanocrystals in situ at specific locations along the tubular member 200.

In some embodiments, it is possible to achieve equal to or greater than 0.5 mW of UV intensity by combining the output of multiple LEDs (e.g., 2-5 LEDs) through the use of dichroic minors as described below. Some embodiments include multiple LEDs transmitting UV light having different wavelengths.

Figure 5:
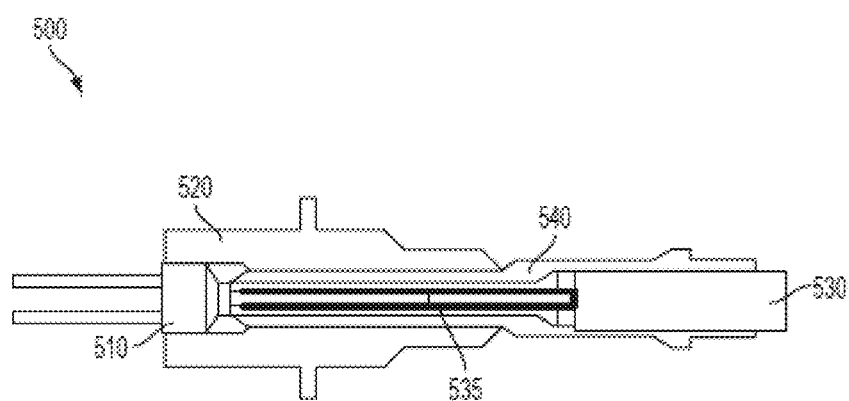
FIG. 5 is a block diagram that illustrates an example of a UV illumination coupler, according to an embodiment.

FIG. 5 is a block diagram that illustrates an example of a UV light coupling system 500, for use with various embodiments. In this non-limiting embodiment, the system 500 comprises an LED 510, a housing 520, a fiber core 535, a cable housing 540 and a fiber cable 530.

Figure 6A:
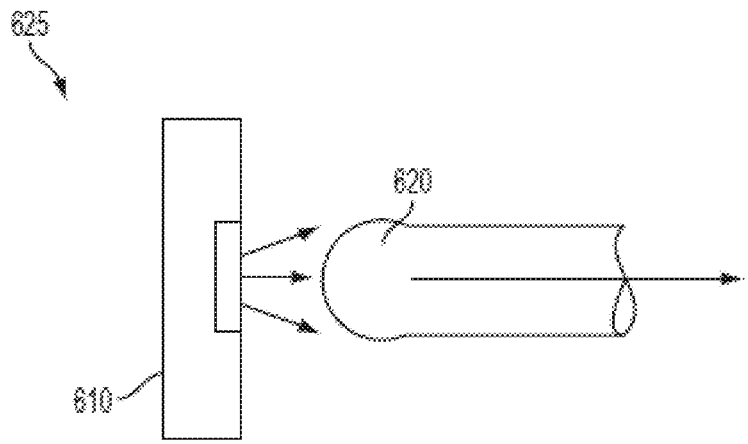
FIGS. 6A-6B are block diagrams that illustrate examples of UV illumination coupling systems, according to embodiments.
Figure 6B:
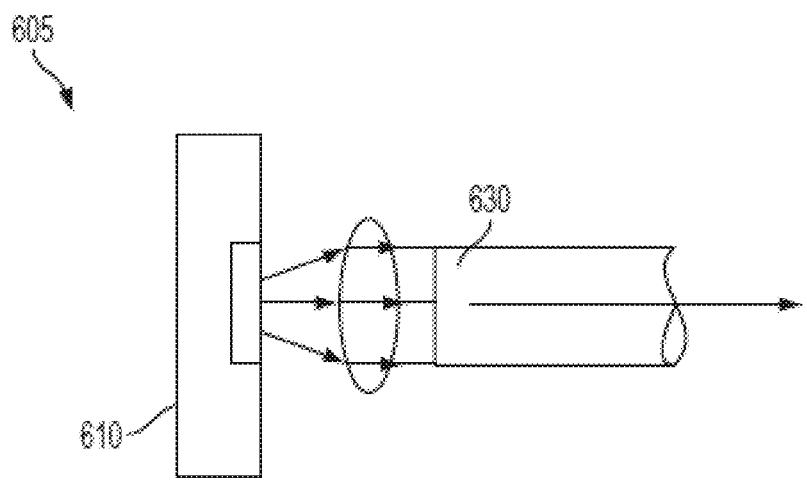

FIGS. 6A and 6B are block diagrams that illustrate examples of UV light coupling systems 600 and 605, according to embodiments, for coupling the LED output of the LED 610 to optical fiber 240. The LED 310 may be end-coupled with a spherical-ended fiber 620 as shown in FIG. 6A, or it may be lens-coupled with a flat-ended fiber 630 as shown in FIG. 6B.

FIGS. 7A-7D are block diagrams that illustrate examples of UV-fiber couplers 325, according to embodiments, for coupling the LED output of the LED 310 to optical fiber 240.

Figure 7A:
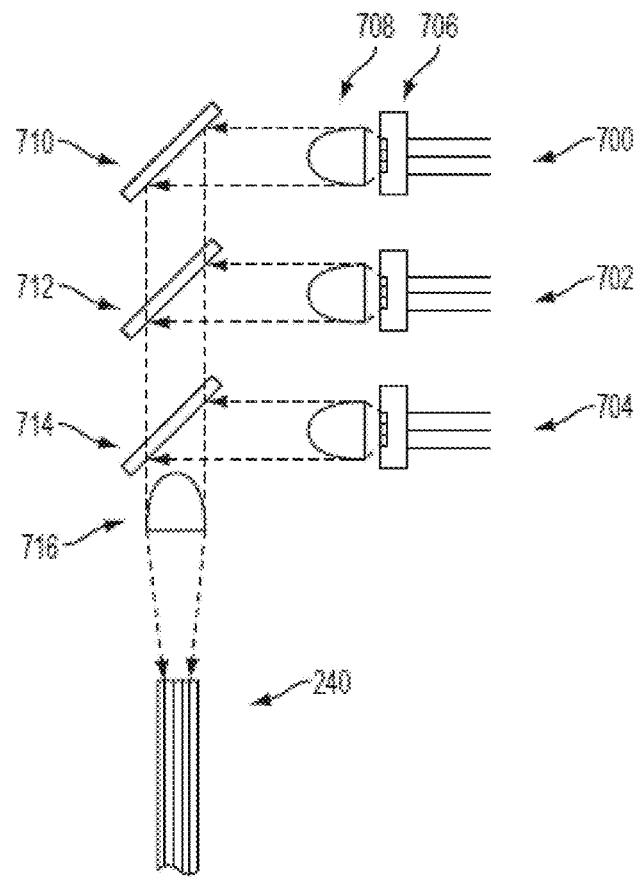
FIGS. 7A-7D are block diagrams that illustrate examples of UV illumination couplings, according to embodiments.

FIG. 7A shows an embodiment wherein a group of LEDs 706 having differing wavelengths including a 275 nm LED 700, a 265 nm LED 702, and a 255 nm LED 704. Each of these LEDs includes a diode 706 and a lens 708. The coupling system of FIG. 7A includes dichroic minors 710, 712, 714 for each of the individual LEDs 700, 702, 704. The dichroic minors 710, 712, 714 direct UV light from each LED 700, 702, 704 into an output lens 716 which focuses the combined beams into the optical fiber or bundle 740. In some embodiments, the cutoff wavelengths of the individual dichroic mirrors may be set between the output of the individual LEDs 706. For example, in one non-limiting embodiment, the longpass dichroic mirrors 710, 712 and 714 of FIG. 7A have cutoff wavelengths of 280 nm, 270 nm and 260 nm, respectively. Other embodiments may employ a higher number of individual LEDs (e.g., 5 LEDs) to cover wavelengths between about 250 nm and 300 nm. Although the LEDs 700, 702, 704 depicted in FIG. 7A are shown as surface emitting LEDs, other types of LEDs such as canister LEDs may also be employed.

Figure 7B:
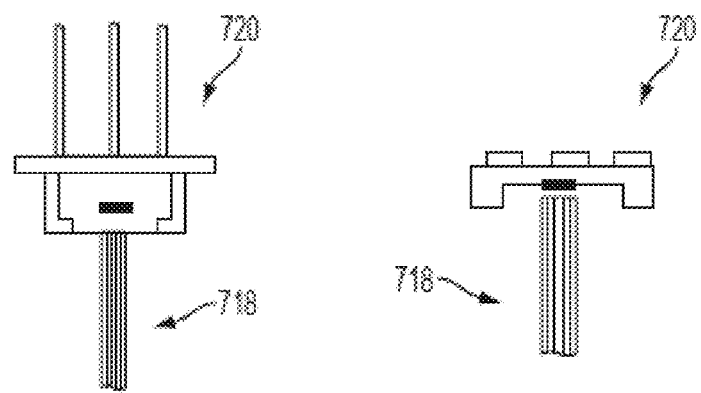

FIG. 7B shows another embodiment for coupling the LED output of the UV source 310 to optical fiber 240, wherein a fiber or fiber bundle 718 is in direct contact with an individual LED 720. This direct-contact arrangement can be well suited for surface emitting LEDs in which the fiber/fiber bundle 718 can be positioned directly over the LED emitter. This arrangement can be well suited if the numerical aperture of the optical fiber 240 is high and the diameter of the optical fiber or bundle 240 is large because such arrangement promotes high coupling efficiency. In such embodiments, the UV coupler is the contact point between the optical fiber and the LED as UV source. Non-limiting examples of direct-contact couplers include SC and ST style couplers.

Figure 7C:
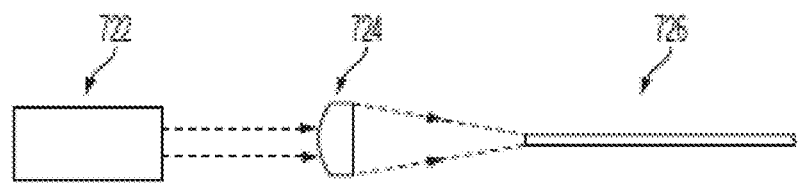
Figure 7D:
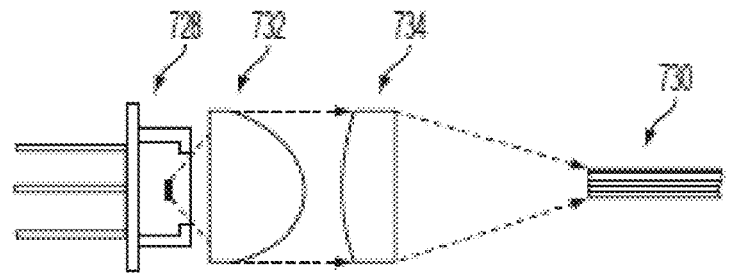

FIG. 7C shows another embodiment for coupling the output from a laser diode 722 to an optical fiber/bundle 726 via a lens 724. Such embodiments can improve coupling efficiency and reduce power consumption. FIG. 7D shows another embodiment for coupling the output of the LED 728 to an optical fiber bundle 730 in which output of the LED 728 is directed through two separate lenses 732 and 734. In some embodiments, the optical fiber/bundle 730 may be in the form of a bundle of diffusing optical fiber. Diffusing optical fiber can be adapted to control UV leakage by altering, for example, the index of refraction as well as the density and size of scattering particles included within the optical fiber. In some embodiments, a coupling efficiency may be equal to or greater than 80%.

For UV-fiber couplers containing two lenses (e.g., as illustrated in FIGS. 7A and 7D) the first lens (e.g., lens 708, 732) may act as a condenser gathering light transmitted from the UV source to render it close to collimation, and the second lens (e.g., lens 716, 734) may act to focus the collimated beam into the fiber/bundle (e.g., fibers 740, 730). By properly choosing the focal lengths of the lenses and their relative positions to the light source and the fiber bundle, it is possible to control the magnification of the UV light as well as the numerical aperture (e.g., cone angle).

Figure 8:
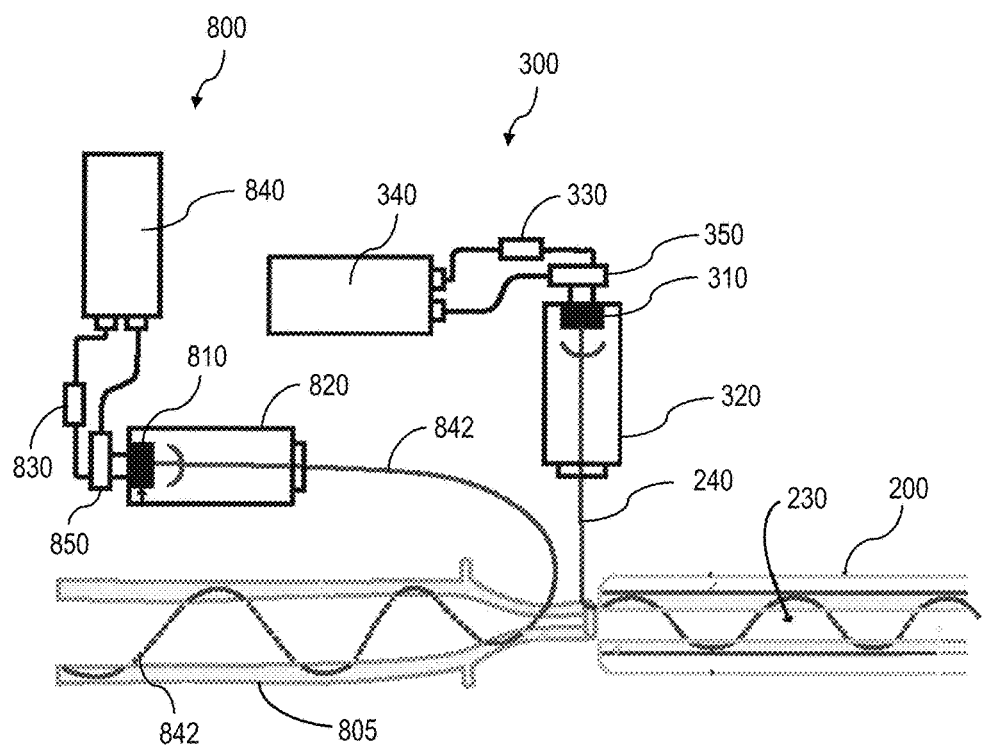
FIG. 8 is a block diagram that illustrates an example of a UV illuminated collection bag attached to a UV illuminated tubular member, according to one embodiment.

In some embodiments, a collection bag 400 adapted for use with an indwelling catheter 100 of the present invention may also be irradiated using UV light. FIG. 8 is a block diagram that illustrates an example of a UV illuminated collection bag attached to a UV illuminated tubular member, according to one embodiment. In this example a separate UV illumination system 800 may be used to transmit UV radiation into a collection bag 805. The example catheter system of FIG. 8 includes a UV illumination system 300 providing ultraviolet radiation to catheter tube 200 and a UV illumination system 800 providing ultraviolet radiation to a collection bag 805. The UV illumination system 800 of FIG. 8 comprises an LED 810 housed in an LED fiber coupler housing 820 used to illuminate an optical fiber 842 which traverses at least a portion of the collection bag 805. An LED socket 850 connects the LED 810 to a power source 840 and a current controller 830. In some embodiments, the power source 840 may be in the form of a battery; although any other power source capable of generating the required current to power the LED 810 may be used. In other embodiments, the same UV source may be used to illuminate the lumen of the indwelling catheter as well as the collection bag or tubing. Reflective cladding is not essential for the optical fiber used to sterilize the collection bag, because the bag is not in contact with healthy tissue of the subject.

In some embodiments, the UV illumination system 800 may be operated by a controller 360 (see FIG. 3) such as by a chip set as described below and illustrated in FIG. 9 or a software configured general purpose computer as described below and illustrated in FIG. 10.

Figure 9:
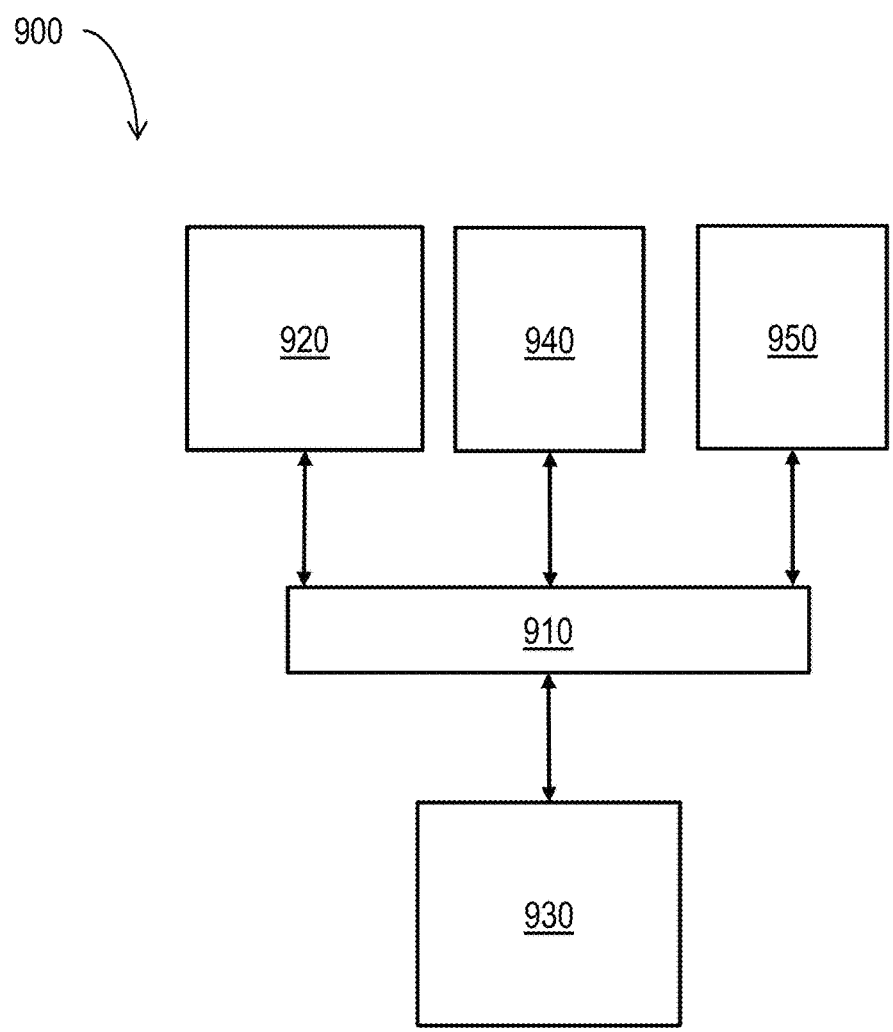
FIG. 9 is a block diagram that illustrates a chip set upon which an embodiment of the invention may be implemented.

FIG. 9 illustrates a chip set 900 upon which an embodiment of the invention may be implemented. Chip set 900 is programmed to perform one or more steps of a method described herein and includes, for instance, the processor and memory components described with respect to FIG. 9 incorporated in one or more physical packages (e.g., chips). By way of example, a physical package includes an arrangement of one or more materials, components, and/or wires on a structural assembly (e.g., a baseboard) to provide one or more characteristics such as physical strength, conservation of size, and/or limitation of electrical interaction. It is contemplated that in certain embodiments the chip set can be implemented in a single chip. Chip set 900, or a portion thereof, constitutes a means for performing one or more steps of a method described herein.

In one embodiment, the chip set 900 includes a communication mechanism such as a bus 910 for passing information among the components of the chip set 900. A processor 920 has connectivity to the bus 910 to execute instructions and process information stored in, for example, a memory 930. The processor 920 may include one or more processing cores with each core configured to perform independently. A multi-core processor enables multiprocessing within a single physical package. Examples of a multi-core processor include two, four, eight, or greater numbers of processing cores. Alternatively or in addition, the processor 920 may include one or more microprocessors configured in tandem via the bus 910 to enable independent execution of instructions, pipelining, and multithreading. The processor 920 may also be accompanied with one or more specialized components to perform certain processing functions and tasks such as one or more digital signal processors (DSP) 940, or one or more application-specific integrated circuits (ASIC) 950. A DSP 940 typically is configured to process real-world signals (e.g., sound) in real time independently of the processor 920. Similarly, an ASIC 950 can be configured to performed specialized functions not easily performed by a general purposed processor. Other specialized components to aid in performing the inventive functions described herein include one or more field programmable gate arrays (FPGA) (not shown), one or more controllers (not shown), or one or more other special-purpose computer chips.

The processor 920 and accompanying components have connectivity to the memory 930 via the bus 910. The memory 930 includes both dynamic memory (e.g., RAM, magnetic disk, writable optical disk, etc.) and static memory (e.g., ROM, CD-ROM, etc.) for storing executable instructions that when executed perform one or more steps of a method described herein. The memory 910 also stores the data associated with or generated by the execution of one or more steps of the methods described herein.

Although processes, equipment, and data structures are depicted in FIG. 9 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

Figure 10:
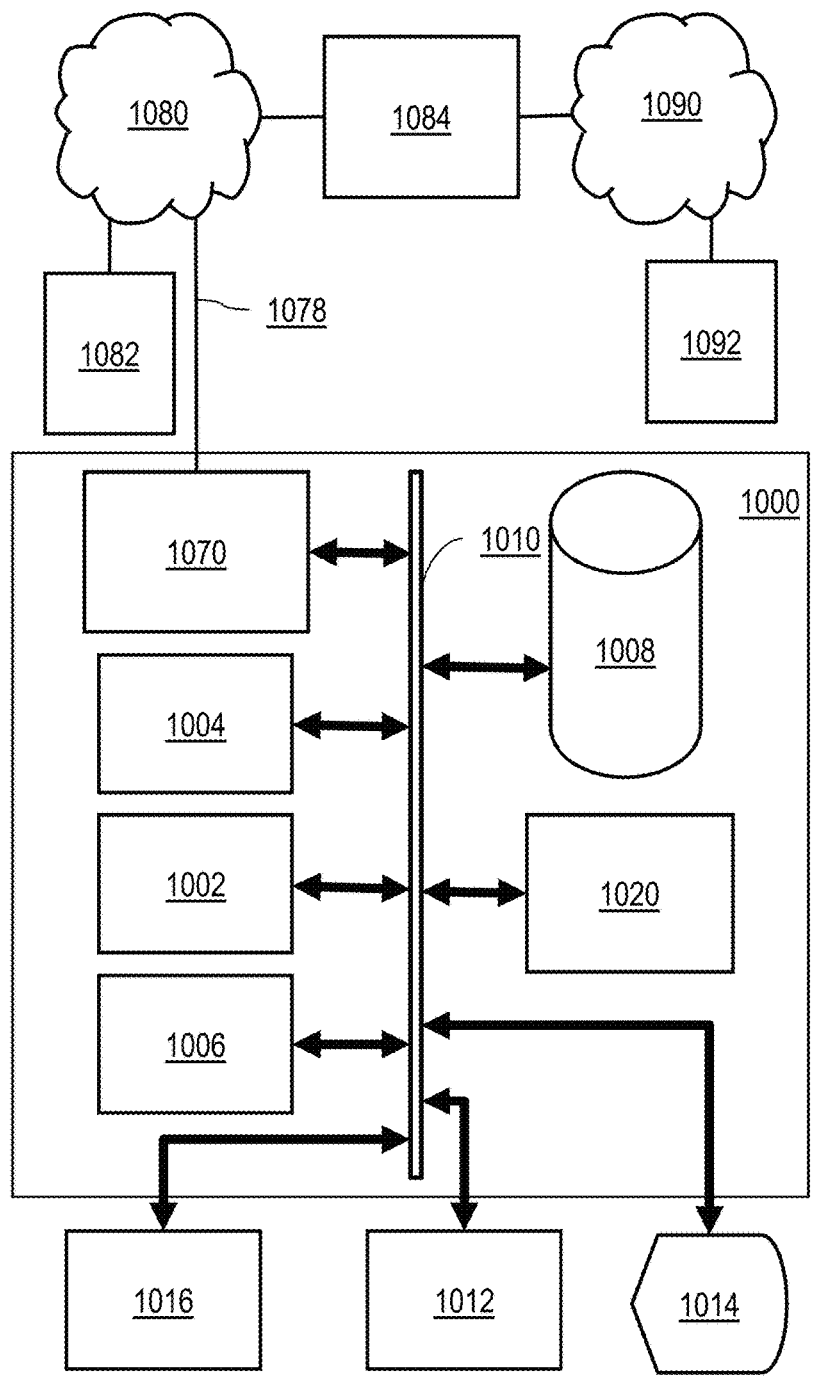
FIG. 10 is a block diagram that illustrates a computer system upon which an embodiment of the invention may be implemented.

FIG. 10 is a block diagram that illustrates a computer system 1000 upon which an embodiment of the invention may be implemented. Computer system 1000 includes a communication mechanism such as a bus 1010 for passing information between other internal and external components of the computer system 1000. Information is represented as physical signals of a measurable phenomenon, typically electric voltages, but including, in other embodiments, such phenomena as magnetic, electromagnetic, pressure, chemical, molecular atomic and quantum interactions. For example, north and south magnetic fields, or a zero and non-zero electric voltage, represent two states (0, 1) of a binary digit (bit). Other phenomena can represent digits of a higher base. A superposition of multiple simultaneous quantum states before measurement represents a quantum bit (qubit). A sequence of one or more digits constitutes digital data that is used to represent a number or code for a character. In some embodiments, information called analog data is represented by a near continuum of measurable values within a particular range. Computer system 1000, or a portion thereof, constitutes a means for performing one or more steps of one or more methods described herein.

A sequence of binary digits constitutes digital data that is used to represent a number or code for a character. A bus 1010 includes many parallel conductors of information so that information is transferred quickly among devices coupled to the bus 1010. One or more processors 1002 for processing information are coupled with the bus 1010. A processor 1002 performs a set of operations on information.

The set of operations include bringing information in from the bus 1010 and placing information on the bus 1010. The set of operations also typically include comparing two or more units of information, shifting positions of units of information, and combining two or more units of information, such as by addition or multiplication. A sequence of operations to be executed by the processor 1002 constitutes computer instructions.

Computer system 1000 also includes a memory 1004 coupled to bus 1010. The memory 1004, such as a random access memory (RAM) or other dynamic storage device, stores information including computer instructions. Dynamic memory allows information stored therein to be changed by the computer system 1000. RAM allows a unit of information stored at a location called a memory address to be stored and retrieved independently of information at neighboring addresses. The memory 1004 is also used by the processor 1002 to store temporary values during execution of computer instructions. The computer system 1000 also includes a read only memory (ROM) 1006 or other static storage device coupled to the bus 1010 for storing static information, including instructions, that is not changed by the computer system 1000. Also coupled to bus 1010 is a non-volatile (persistent) storage device 1008, such as a magnetic disk or optical disk, for storing information, including instructions, that persists even when the computer system 1000 is turned off or otherwise loses power.

Information, including instructions, is provided to the bus 1010 for use by the processor from an external input device 1012, such as a keyboard containing alphanumeric keys operated by a human user, or a sensor. A sensor detects conditions in its vicinity and transforms those detections into signals compatible with the signals used to represent information in computer system 1000. Other external devices coupled to bus 1010, used primarily for interacting with humans, include a display device 1014, such as a cathode ray tube (CRT) or a liquid crystal display (LCD), for presenting images, and a pointing device 1016, such as a mouse or a trackball or cursor direction keys, for controlling a position of a small cursor image presented on the display 1014 and issuing commands associated with graphical elements presented on the display 1014.

In the illustrated embodiment, special purpose hardware, such as an application specific integrated circuit (IC) 1020, is coupled to bus 1010. The special purpose hardware is configured to perform operations not performed by processor 1002 quickly enough for special purposes. Examples of application specific ICs include graphics accelerator cards for generating images for display 1014, cryptographic boards for encrypting and decrypting messages sent over a network, speech recognition, and interfaces to special external devices, such as robotic arms and medical scanning equipment that repeatedly perform some complex sequence of operations that are more efficiently implemented in hardware.

Computer system 1000 also includes one or more instances of a communications interface 1070 coupled to bus 1010. Communication interface 1070 provides a two-way communication coupling to a variety of external devices that operate with their own processors, such as printers, scanners and external disks. In general the coupling is with a network link 1078 that is connected to a local network 1080 to which a variety of external devices with their own processors are connected. For example, communication interface 1070 may be a parallel port or a serial port or a universal serial bus (USB) port on a personal computer. In some embodiments, communications interface 1070 is an integrated services digital network (ISDN) card or a digital subscriber line (DSL) card or a telephone modem that provides an information communication connection to a corresponding type of telephone line. In some embodiments, a communication interface 1070 is a cable modem that converts signals on bus 1010 into signals for a communication connection over a coaxial cable or into optical signals for a communication connection over a fiber optic cable. As another example, communications interface 1070 may be a local area network (LAN) card to provide a data communication connection to a compatible LAN, such as Ethernet. Wireless links may also be implemented. Carrier waves, such as acoustic waves and electromagnetic waves, including radio, optical and infrared waves travel through space without wires or cables. Signals include man-made variations in amplitude, frequency, phase, polarization or other physical properties of carrier waves. For wireless links, the communications interface 1070 sends and receives electrical, acoustic or electromagnetic signals, including infrared and optical signals, that carry information streams, such as digital data.

The term computer-readable medium is used herein to refer to any medium that participates in providing information to processor 1002, including instructions for execution. Such a medium may take many forms, including, but not limited to, non-volatile media, volatile media and transmission media. Non-volatile media include, for example, optical or magnetic disks, such as storage device 1008. Volatile media include, for example, dynamic memory 1004. Transmission media include, for example, coaxial cables, copper wire, fiber optic cables, and waves that travel through space without wires or cables, such as acoustic waves and electromagnetic waves, including radio, optical and infrared waves. The term computer-readable storage medium is used herein to refer to any medium that participates in providing information to processor 1002, except for transmission media.

Common forms of computer-readable media include, for example, a floppy disk, a flexible disk, a hard disk, a magnetic tape, or any other magnetic medium, a compact disk ROM (CD-ROM), a digital video disk (DVD) or any other optical medium, punch cards, paper tape, or any other physical medium with patterns of holes, a RAM, a programmable ROM (PROM), an erasable PROM (EPROM), a FLASH-EPROM, or any other memory chip or cartridge, a carrier wave, or any other medium from which a computer can read. The term non-transitory computer-readable storage medium is used herein to refer to any medium that participates in providing information to processor 1002, except for carrier waves and other signals.

Logic encoded in one or more tangible media includes one or both of processor instructions on a computer-readable storage media and special purpose hardware, such as ASIC.

Network link 1078 typically provides information communication through one or more networks to other devices that use or process the information. For example, network link 1078 may provide a connection through local network 1080 to a host computer 1082 or to equipment 1084 operated by an Internet Service Provider (ISP). ISP equipment 1084 in turn provides data communication services through the public, world-wide packet-switching communication network of networks now commonly referred to as the Internet 1090. A computer called a server 1092 connected to the Internet provides a service in response to information received over the Internet. For example, server 1092 provides information representing video data for presentation at display 1014.

The invention is related to the use of computer system 1000 for implementing the techniques described herein. According to one embodiment of the invention, those techniques are performed by computer system 1000 in response to processor 1002 executing one or more sequences of one or more instructions contained in memory 1004. Such instructions, also called software and program code, may be read into memory 1004 from another computer-readable medium such as storage device 1008. Execution of the sequences of instructions contained in memory 1004 causes processor 1002 to perform the method steps described herein. In alternative embodiments, hardware, such as application specific integrated circuit 1020, may be used in place of or in combination with software to implement the invention. Thus, embodiments of the invention are not limited to any specific combination of hardware and software.

The signals transmitted over network link 1078 and other networks through communications interface 1070, carry information to and from computer system 1000. Computer system 1000 can send and receive information, including program code, through the networks 1080, 1090 among others, through network link 1078 and communications interface 1070. In an example using the Internet 1090, a server 1092 transmits program code for a particular application, requested by a message sent from computer 1000, through Internet 1090, ISP equipment 1084, local network 1080 and communications interface 1070. The received code may be executed by processor 1002 as it is received, or may be stored in storage device 1008 or other non-volatile storage for later execution, or both. In this manner, computer system 1000 may obtain application program code in the form of a signal on a carrier wave.

Various forms of computer readable media may be involved in carrying one or more sequence of instructions or data or both to processor 1002 for execution. For example, instructions and data may initially be carried on a magnetic disk of a remote computer such as host 1082. The remote computer loads the instructions and data into its dynamic memory and sends the instructions and data over a telephone line using a modem. A modem local to the computer system 1000 receives the instructions and data on a telephone line and uses an infra-red transmitter to convert the instructions and data to a signal on an infra-red a carrier wave serving as the network link 1078. An infrared detector serving as communications interface 1070 receives the instructions and data carried in the infrared signal and places information representing the instructions and data onto bus 1010. Bus 1010 carries the information to memory 1004 from which processor 1002 retrieves and executes the instructions using some of the data sent with the instructions. The instructions and data received in memory 1004 may optionally be stored on storage device 1008, either before or after execution by the processor 1002.

Although processes, equipment, and data structures are depicted in FIG. 10 as integral blocks in a particular arrangement for purposes of illustration, in other embodiments one or more processes or data structures, or portions thereof, are arranged in a different manner, on the same or different hosts, in one or more databases, or are omitted, or one or more different processes or data structures are included on the same or different hosts.

Figure 11:
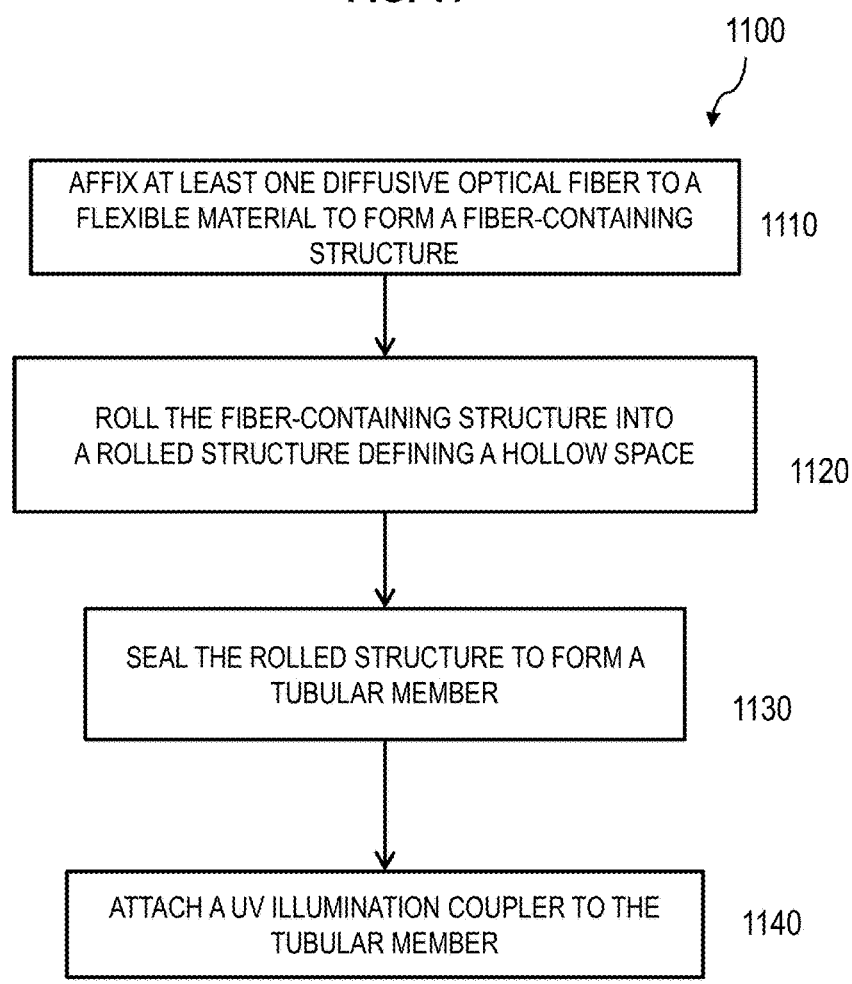
FIG. 11 is a flow chart that illustrates an example method for producing a device of the present disclosure, according to an embodiment.

Devices of the present disclosure may contain the UV illumination system 300 and the tubular member 200 as described above. FIG. 11 is a flow chart that illustrates an example method 1100 for producing a device of the present disclosure, according to an embodiment. Although steps are depicted in FIG. 11, and later flow chart FIG. 12, as integral steps in a particular order for purposes of illustration, in other embodiments, one or more steps, or portions thereof, are performed in a different order, or overlapping in time, in series or in parallel, or are omitted, or one or more additional steps are added, or the method is changed in some combination of ways.

In step 1110 at least one optical fiber 240 is affixed to a flexible material to form a fiber-containing structure. In step 1120 the fiber-containing structure is rolled to form a rolled structure defining a hollow space corresponding to the longitudinal interior space of the lumen 230. In step 1130 the rolled structure is sealed to form the tubular member 200. In step 1140 the UV illumination system 300 is attached to the tubular member 200 to form the device. Some embodiment may include an additional step of depositing a layer of a reflective metal (e.g., Al, Ti) onto at least a portion of the flexible material to provide a UV-reflective layer 250.

Figure 12:
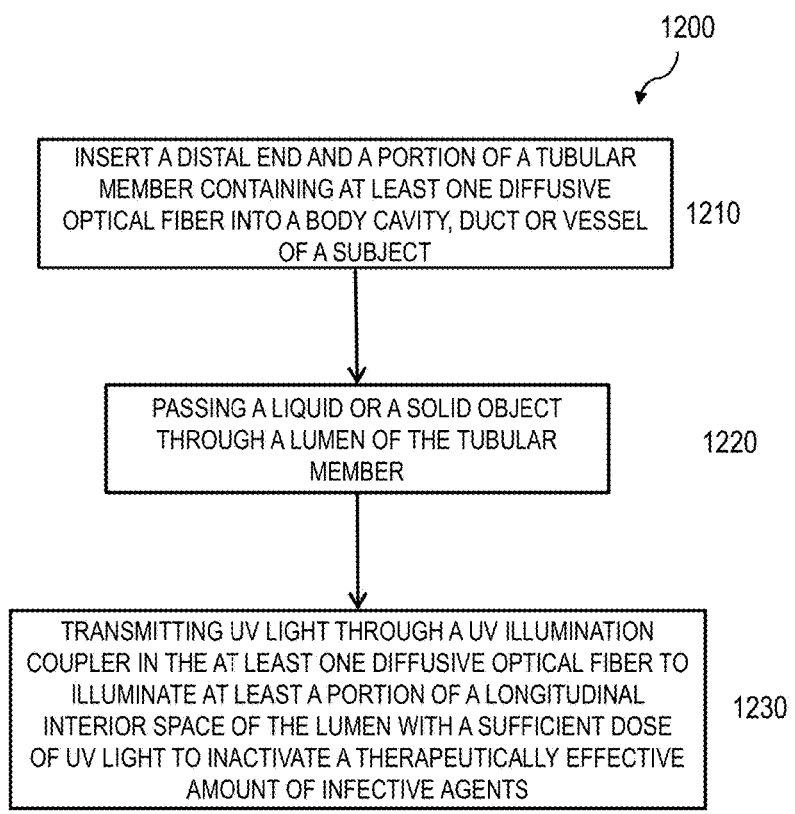
FIG. 12 is a flow chart that illustrates an example treatment method, according to an embodiment.

FIG. 12 is a flow chart that illustrates an example treatment method 1200, according to an embodiment. In step 1210, a distal end and a portion of the tubular member 200 are inserted into a body cavity, duct or vessel of a subject. In step 1220, a liquid or solid object is passes through the lumen 230. In step 1230, UV light is transmitted through the UV illumination coupler 320 to illuminate at least a portion of the longitudinal interior space with a sufficient dose of UV light to inactivate a therapeutically effective amount of infective agents, e.g., down to about 10% of an original population of agents.

It is anticipated that, in some embodiments, a dosage of the UV light is effective to inactivate infective agents contained in the lumen 230 by four orders of magnitude while producing no measurable UV-induced damage to DNA contained in tissues of the subject. UV dose is defined as the radiance of the UV light multiplied by the time period of exposure to the UV light, as expressed mathematically in formula (I) below:

$$UV \text{ Dose} \left(\frac{mJ}{cm^2}\right) = UV \text{ Radiance} \left(\frac{mW}{cm^2}\right) \times \text{Time}(s) \quad (I)$$

A corresponding radiance provided by the UV source 310 to generate the UV dose within the lumen 230 will further depend upon the coupling efficiency of the UV-fiber coupler 325, as explained above. A corresponding radiance of the UV source equals the radiance of UV light received by the one or more optical fiber divided by the coupling efficiency of the UV-fiber coupler 325, as expressed mathematically in formula (II) below:

$$\text{Radiance of } UV \text{ Source} \left(\frac{mJ}{cm^2}\right) = \frac{UV \text{ Radiance} \left(\frac{mJ}{cm^2}\right)}{\text{Coupling Efficiency}} \quad (II)$$

In some embodiments, a UV dose that is sufficient to inactivate a therapeutically effective amount of infective agents contained in the lumen 230 ranges from about 0.5 mJ/cm$^2$ to about 200 mJ/cm$^2$, relative to a radiance necessary to inactivate infective agents over a time period of 1 second. In other embodiments, the UV dose is from about 1 mJ/cm$^2$ to about 80 mJ/cm$^2$. In still other embodiments, the UV dose is from about 5 mJ/cm$^2$ to about 30 mJ/cm$^2$. These doses can be delivered continuously or intermittently, such as for example by a low radiance for a continuous time or a higher radiance applied for a shorter time, with repeat times based on the rate that fluid or particles pass through the lumen of the tubular structure. UV doses may be applied using UV light having wavelengths of less than about 300 nm. In other embodiments the UV light may have a wavelength between about 250 nm and about 300 nm. Some embodiments employ UV light having a wavelength of about 250 nm.

Figure 15:
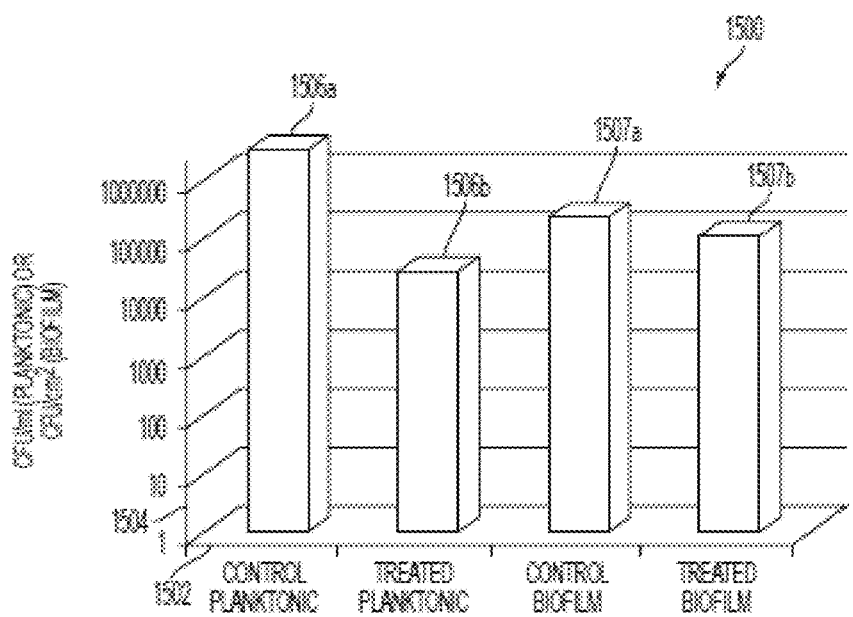
FIG. 15 is a chart plotting microorganism concentrations, according to various experiments.

FIG. 15 is chart 1500 plotting microorganism concentrations 1504 (in colony forming units (CPU) for a number of experiments both with and without UV illumination according to various embodiments. These non-optimized, proof-of-concept experimental embodiments employed a UV illumination system as shown in FIG. 3C, including a UV-fiber coupler 325 as illustrated in FIG. 7D. The UV source 310 was a 0.3 microwatt 265 nm LED. The coupler 325 of FIG. 7D included two lenses 732, 734 to transmit UV light output into an optical fiber bundle 730 made up of diffusive optical fibers. The optical fiber bundle 730 was placed inside of a lumen 230 (1 m section of size 16 silicon tubing, 7 ml interior volume) seeded with a bacteria sample, and the interior space of the lumen 230 was illuminated continuously for 24 hours. In control experiments the optical fiber bundle 730 was placed inside of the bacteria-seeded lumen for 8 hours without any UV illumination.

The bacteria samples were prepared by culturing *E. coli* for 8 hours at 37° C. with shaking in synthetic urine (see Davis et al., "In vivo reduction of bacterial populations in the urinary tract of cathetized sheep by iontophoresis" *J. Urol.*, 1995, 154(5), 1948-53 and Davis et al., "Quantification, qualification, and microbial killing efficiencies of anti-microbial chlorine-based substances produced by iontophoresis" *Antimicrobial Agents and Chemotherapy*, 1994, 38(12), 2768-74). The resulting cultures were then diluted in fresh synthetic urine and bacterial samples were grown until they had attained logarithmic growth phases. Aliquots of such logarithmic phase cultures (1×10E8 CFU/ml) were then injected into the lumens (100 μl) and allowed to attach for 30 minutes. For each experiment the UV diode 310 was then attached to the diffusive optical fiber bundle 730 and was activated to transmit UV light down the diffusing optical fiber bundle 730. Following UV light application (24 hours), bacterial samples were obtained from free-floating populations (planktonic bacteria) by aspiration of the suspended fluid. Biofilm samples were obtained by scraping the interior walls 220 of the lumens 230. All resulting samples were then homogenized (25K/min) to break apart the adherent biofilm communities for accurate CFU determination, followed by serial dilution and plating for determination of viable bacterial numbers 6-9.10, 11.12, 13.3, 12. All samplings were performed in triplicate.

Columns 1506*a* and 1506*b* of FIG. 15 illustrate the effect of the UV illumination and control experiments using a planktonic sample. It was observed by comparing the control experiment 1506*a* to the embodiment experiment 1506*b* that UV illumination using this embodiment reduces the planktonic concentration by about two orders of magnitude. Columns 1507*a* and 1507*b* illustrate the effect of UV illumination according to the embodiment on a biofilm sample. It was observed by comparing the control experiment 1507*a* to the embodiment experiment 1507*b* that UV illumination using the device of the present disclosure reduces biofilm concentration by about 15 to 20 percent. In other embodiments it is possible to effect greater reductions in microorganism concentration by altering the placement and/or shape of the optical fiber(s), or by altering the wavelength, intensity and/or periodicity of the UV light transmitted through the optical fiber(s).

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense. Throughout this specification and the claims, unless the context requires otherwise, the word "comprise" and its variations, such as "comprises" and "comprising," will be understood to imply the inclusion of a stated item, element or step or group of items, elements or steps but not the exclusion of any other item, element or step or group of items, elements or steps. Furthermore, the indefinite article "a" or "an" is meant to indicate one or more of the item, element or step modified by the article. The term substantively means all but a negligible amount of a property of an item, element, step or group.

What is claimed is:

1. A device, comprising a tubular member, wherein the tubular member is flexible and configured to receive ultraviolet (UV) light from a UV illumination coupler, the tubular member comprising:
    a lumen defining a longitudinal interior space within the tubular member;
    a tubular body bounded by
        an inner wall facing the longitudinal interior space and defining an outer boundary of the lumen, and
        an outer wall defining an outer surface of the tubular member;
    at least one optical fiber disposed on the inner wall facing the longitudinal interior space and outside of the interior space not parallel to an axis of the lumen and adapted to receive the UV light from the UV illumination coupler and to emit UV light into the lumen along at least a portion of a length of the lumen; and
    a protective component adapted to prevent substantively all of the UV light emitted from the optical fiber from exiting the outer wall.

2. The device of claim 1, wherein:
    the protective component is a UV reflective material disposed between the at least one optical fiber and the outer wall; or
    the protective component is a UV reflective coating forming the outer wall.

3. The device of claim 2, wherein the UV reflective material or UV reflective coating comprises at least one selected from the group comprising titanium, aluminum, chromium, iron, nickel, copper, zinc, palladium, silver, platinum and gold.

4. The device of claim 1, wherein:
    the tubular body comprises a UV transmissive inner section comprising the optical fiber embedded in a UV transmissive material and situated at or near the inner wall; and
    the protective component comprises a UV absorbent outer section comprising a UV absorbent material situated at or near the outer wall.

5. The device of claim 4, wherein the UV transmissive material is a silicone.

6. The device of claim 4, wherein the UV absorbent material is a plastic commonly used in catheters.

7. The device of claim 1, wherein the optical fiber is a diffusive optical fiber.

8. The device of claim 1, wherein the optical fiber is a non-diffusive diffusive optical fiber configured to terminate at the portion of the length of the lumen to be illuminated.

9. The device of claim 1, wherein the optical fiber is a bundle of optical fibers.

10. The device of claim 1, wherein the optical fiber is disposed in a spiral configuration that is substantively coaxial with the lumen.

11. The device of claim 1, further comprising:
a port in fluid communication with the lumen and situated at a proximal end of the tubular member; and
an opening in fluid communication with the lumen and situated at a distal end of the tubular member.

12. The device of claim 1, further comprising at least one light source adapted to emit the UV light to illuminate the UV illumination coupler.

13. The device of claim 12, further comprising:
a power source;
a power socket adapted to transmit current from the power source to the light source; and
a current controller adapted to control current from the power source to the light source.

14. The device of claim 12, wherein the light source is adapted to emit the UV light having a frequency of about 250 nm to about 300 nm.

15. The device of claim 12, wherein the light source is selected from a group comprising a light emitting diode (LED), a laser diode (LD), a superluminescent light emitting diode (SLED), a nanodot LED, a quantum dot, a laser and a combination thereof.

16. A device, comprising a tubular member, wherein the tubular member is flexible and configured to receive ultraviolet (UV) light from a UV illumination coupler, the tubular member comprising:
a lumen defining a longitudinal interior space within the tubular member;
a tubular body bounded by
an inner wall facing the longitudinal interior space and defining an outer boundary of the lumen, and
an outer wall defining an outer surface of the tubular member;
at least one optical fiber disposed outside of the interior space not parallel to an axis of the lumen and adapted to receive the UV light from the UV illumination coupler and to emit UV light into the lumen along at least a portion of a length of the lumen;
a protective component adapted to prevent substantively all of the UV light emitted from the optical fiber from exiting the outer wall; and
a collection bag adapted to receive a liquid from the lumen, wherein the collection bag comprises at least one collection bag optical fiber adapted to emit UV light into an interior space of the collection bag.

17. A method for producing the device of claim 1, the method comprising:
affixing the at least one optical fiber to a flexible material to form a fiber-containing structure;
rolling the fiber-containing structure to form a rolled structure defining a hollow space corresponding to the longitudinal interior space;
sealing the rolled structure to form the tubular member; and
attaching the ultraviolet illumination coupler to the tubular member.

18. A treatment method using a device comprising a tubular member, wherein the tubular member is flexible and configured to receive ultraviolet (UV) light from a UV illumination coupler, the tubular member comprising a lumen defining a longitudinal interior space within the tubular member, a tubular body bounded by an inner wall facing the longitudinal interior space and defining an outer boundary of the lumen and an outer wall defining an outer surface of the tubular member, at least one optical fiber disposed outside of the interior space not parallel to an axis of the lumen and adapted to receive the UV light from the UV illumination coupler and to emit UV light into the lumen along at least a portion of a length of the lumen and a protective component adapted to prevent substantively all of the UV light emitted from the optical fiber from exiting the outer wall, the method comprising:
inserting a distal end and a portion of the tubular member into a body cavity, duct or vessel of a subject;
passing a liquid or a solid object through the lumen; and
transmitting the UV light through the UV illumination coupler to illuminate at least a portion of the longitudinal interior space with a sufficient dose of UV light to inactivate a therapeutically effective amount of infective agents.

19. The treatment method of claim 18, wherein the therapeutically effective amount is a reduction of bacteria contained in the lumen by at least two orders of magnitude while producing no measurable UV-induced damage in tissues of the subject.

* * * * *